United States Patent [19]

Hoffman et al.

[11] Patent Number: 5,439,288
[45] Date of Patent: Aug. 8, 1995

[54] AUTOMATED SMALL VOLUME RECIRCULATOR FOR PARTICLE ANALYSIS

[75] Inventors: Jeffrey G. Hoffman, Hatfield; Mary E. Gerrard, New Britain; Alex H. Clark, Sigel, all of Pa.

[73] Assignee: General Signal Corporation, Stamford, Conn.

[21] Appl. No.: 189,864

[22] Filed: Feb. 1, 1994

[51] Int. Cl.⁶ .................... B01F 15/02/11/02
[52] U.S. Cl. .................... 366/137; 366/117; 366/127; 366/142; 366/153.1; 366/167.1
[58] Field of Search ............ 366/132, 134, 136, 137, 366/142, 143, 151, 153, 159, 108, 117, 127; 73/290 R, 291

[56] References Cited

U.S. PATENT DOCUMENTS

| | | | |
|---|---|---|---|
| 1,992,938 | 3/1935 | Chambers | 366/108 |
| 4,071,225 | 1/1978 | Holl | 366/127 |
| 4,362,033 | 12/1982 | Young | 366/153 |
| 4,474,476 | 10/1984 | Thomsen | 366/153 |
| 4,823,277 | 9/1989 | Neal | 366/137 |
| 4,823,987 | 4/1989 | Switall | 366/142 |

*Primary Examiner*—Robert W. Jenkins
*Attorney, Agent, or Firm*—Milton E. Kleinman; Raymond E. Smiley; Robert S. Smith

[57] ABSTRACT

A mixing and delivery system for supplying small particles suspended in a liquid to form a slurry for delivery and recirculation which includes a mixing tank having an inlet and an outlet, a pump having an inlet and an outlet, a sample cell having an inlet and an outlet, an ultrasonic flow cell having an inlet and an outlet, and a transition bushing having an inlet and an outlet. The sample cell has first and second generally rectangular planar opposed faces, the inlet of the sample cell is rectangular and defined by two opposed sides which are respectively part of the first and second generally rectangular planar opposed faces. The opposed sides are much longer in length than the intermediate opposed sides of the rectangular inlet. The outlet of the mixing tank is connected to the inlet of the pump and the outlet of the pump is connected to the inlet of the transition bushing by a circular cross section tube, that is coupled directly to the inlet of the sample cell. The transition bushing has a tapered construction and the transition bushing tapers at the inlet thereof from the cross-section of the circular cross-section tubing to the rectangular inlet of the sample cell, the transition bushing being formed from (1) a generally trapezoidal shaped portion which tapers from the maximum dimension of the sample cell inlet to the diameter of the tube and (2) two sections of a truncated cone tapering from a maximum circumferential extent proximate the circular cross-section tubing to a point nearer to the sample cell. The ultrasonic flow cell comprises an ultrasonic probe disposed in a fluid conduit between the sample cell and the mixing tank. The conduit forces all of the flow from the sample cell to the mixing tank around the ultrasonic probe.

20 Claims, 3 Drawing Sheets

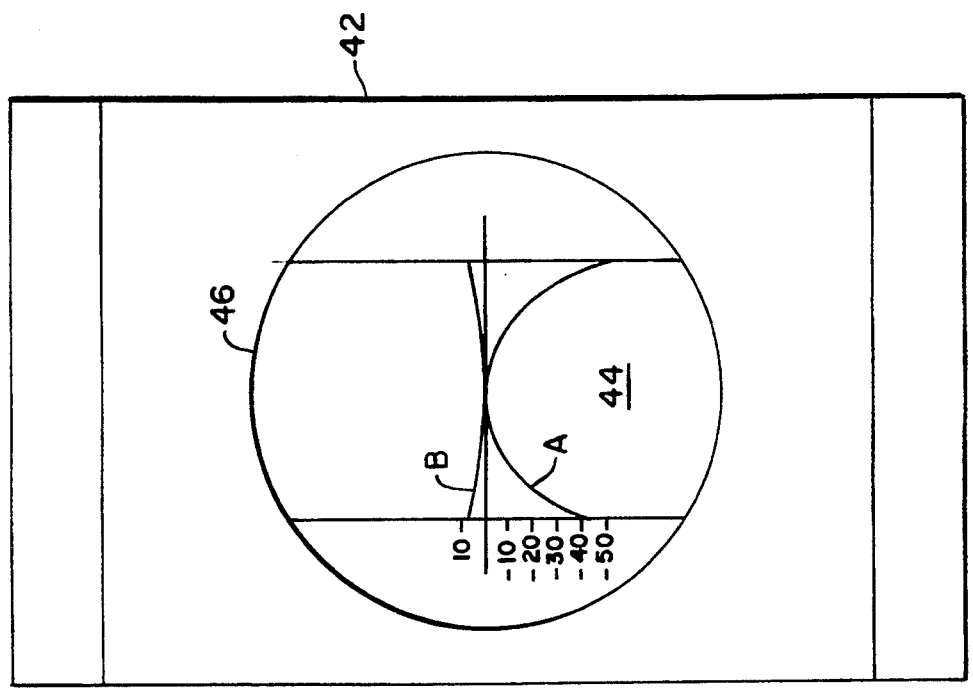
FIG. 3
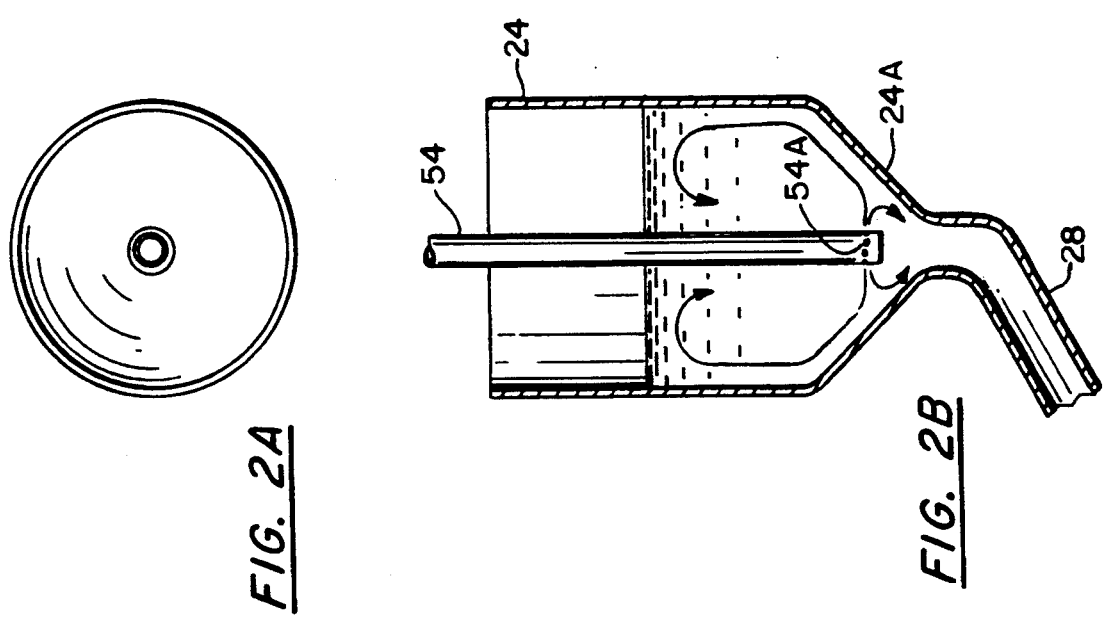
FIG. 2A
FIG. 2B

AUTOMATED SMALL VOLUME RECIRCULATOR FOR PARTICLE ANALYSIS

BACKGROUND OF THE INVENTION

The invention relates to optical particle size apparatus and has particular application to apparatus known as small volume particle size analysis apparatus. Those skilled in the art will recognize that particle size analyses is generally categorized by the collective volume of the mixing tank and circulator apparatus. So called small volume particle size analysis apparatus commonly has a mixing tank and circulator total volume of approximately 300 milliliters. Ultra-small systems are also known which are much smaller as well as larger systems having a combined volume of approximately four liters. Such apparatus has application in many process industries. Examples include process control for the cement, cosmetics and pharmaceutical industries.

The general nature of the present apparatus will be better understood by reference to U.S. Pat. No. 4,496,244 which issued on Jan. 29, 1985 to Albert R. Ludwig and which is assigned to the same assignee as the present application.

In using such apparatus it is common to prepare a slurry by suspending the particles in a liquid and to continually stir the slurry to provide a homogeneous suspension. The slurry is then continually recirculated through the analyzer during analysis.

Typical apparatus of this type utilizes a mixing chamber in which a stirring impeller is disposed to thoroughly mix the particles. The slurry with its suspended particles is pumped from the reservoir or mixing tank to the analyzer and then returned to the reservoir. The apparatus conventionally includes a sample cell. Thus, It is well known that a mixing tank can be utilized with a stirring impeller inserted in the tank to mix the slurry. However, as the mixture is circulated by a pumping action from the tank to an analyzer celt, non-uniformity of distribution and particle settling can occur.

It is of vital importance that the distribution of the particles in the slurry in the sample cell be representative of the entire statistical population. This is obviously necessary to ensure valid data collection for analysis.

A problem in such apparatus is that as the slurry is circulated by a pumping action from the mixing tank to the sample cell there may be a non-uniform distribution of particles in the sample cell.

The prior art has used an ultrasonic probe to provide particle deagglomeration in the mixing tank or before the slurry enters the recirculation apparatus. While this arrangement does produce better particle deagglomeration than apparatus that does not incorporate such ultrasonic probes, the arrangement is still not wholly satisfactory. More particularly it is not satisfactory to apply energy to the entire volume of the reservoir because the energy added to individual particles is not uniform and excessive heat is added to local ares of the slurry.

SUMMARY OF THE INVENTION

It is an object of the invention to provide apparatus which will have a more representative particle distribution in a sample cell of a particle size analysis apparatus than the prior art apparatus.

It is another object of the invention to provide apparatus which will have improved particle deagglomeration than the prior art apparatus.

It is still another object of the invention to provide apparatus which will provide better mixing than conventional impeller type apparatus.

Another object of the invention is provide an ultrasonic apparatus arrangement that will provide substantially equal energy to respective particles.

Still another object of the invention is to provide an ultrasonic apparatus arrangement that will avoid adding excessive heat to the slurry It has now been found that these and other objects of the invention may be attained in a mixing and delivery system for supplying small particles suspended in a liquid to form a slurry for delivery and recirculation which includes a mixing tank having an inlet and an outlet, a pump having an inlet and an outlet, a sample cell having an inlet and an outlet, an ultrasonic flow cell having an inlet and an outlet, and a transition bushing having an inlet and an outlet. The sample cell has first and second generally rectangular planar opposed faces, the inlet of the sample cell is rectangular and defined by two opposed sides which are respectively part of the first and second generally rectangular planar opposed faces. The opposed sides are much longer in length than the intermediate opposed sides of the rectangular inlet. The outlet of the mixing tank is connected to the inlet of the pump and the outlet of the pump is connected to the inlet of the transition bushing by a circular cross section tube, that is coupled directly to the inlet of the sample cell. The transition bushing has a tapered construction and the transition bushing tapers at the inlet thereof from the cross-section of the circular cross-section tubing to the rectangular inlet of the sample cell, the transition bushing being formed from (1) a generally trapezoidal shaped portion which tapers from the maximum dimension of the sample cell inlet to the diameter of the tube and (2) two sections of a truncated cone tapering from a maximum circumferential extent proximate the circular cross-section tubing to a point which is spaced from the circular cross section tubing. The ultrasonic flow cell comprises an ultrasonic probe disposed in a fluid conduit between the sample cell and the mixing tank. The conduit forces all of the flow from the sample cell to the mixing tank around the ultrasonic probe.

In some forms of the invention the ultrasonic flow cell comprises a generally cylindrical housing and the ultrasonic probe is disposed in coaxial relationship with the housing. The mixing tank has a top and a bottom and the bottom may be generally conical. The mixing tank may have a generally vertical axis and the outlet of the flow cell may include a generally elongated tube extending into the mixing tank. The tube may have a free end thereof that extends into the mixing tank and allows fluid flow out of the tube into the mixing tank through a plurality of holes disposed around the side face thereof. The holes in the side face of the tube are disposed in generally axially aligned relationship with the conical portion of the mixing tank in some forms of the invention.

In some forms of the invention the ultrasonic flow cell comprises a generally L-shaped body having first and second generally cylindrical legs and the ultrasonic probe is generally elongated and disposed in generally coaxially relationship with the first cylindrical leg and extends out of the housing proximate to the intersection of the first and second legs. In some embodiments the ultrasonic flow cell has the inlet disposed at an axial extremity of the first leg and the outlet disposed at an axial extremity of the second leg, the first and second legs being in fluid communication.

Other embodiments of the mixing and delivery system for supplying small particles suspended in a liquid to form a slurry for delivery and recirculation comprise a mixing tank having an inlet and an outlet. a pump having an inlet and an outlet, a sample cell having an inlet and an outlet, an ultrasonic flow cell having an inlet and an outlet, a transition bushing having an inlet and an outlet. The sample cell has first and second generally rectangular planar opposed faces and the inlet of the sample cell is rectangular and defined by two opposed sides which are respectively part of the first and second generally rectangular planar opposed faces. The opposed sides are much longer in length than the intermediate opposed sides of the rectangular inlet. The outlet of the mixing tank is connected to the inlet of the pump and the outlet of the pump is connected to the inlet of the transition bushing by a circular cross section tube. The transition bushing is coupled directly to the inlet of the sample cell.

In some forms of the invention the ultrasonic flow cell comprises an ultrasonic probe disposed in a fluid conduit between the sample cell and the mixing tank, the conduit forcing all of the flow from the sample cell to the mixing tank around the ultrasonic probe. The ultrasonic flow cell may comprise a generally cylindrical housing and the ultrasonic probe is disposed in coaxial relationship with the housing and the mixing tank may have a top and a bottom that is generally conical. The mixing tank may have a generally vertical axis and the outlet of the flow cell may include a generally elongated tube extending into the mixing tank having a free end thereof. The free end may extend into the mixing tank and the free end may allow fluid flow out of the tube into the mixing tank through a plurality of holes disposed around the side face thereof. The holes in the side face of the tube are disposed in generally axially aligned relationship with the conical portion of the mixing tank in some forms of the invention.

The ultrasonic flow cell may comprise a generally L-shaped body having first and second generally cylindrical legs and the ultrasonic probe may be generally elongated and disposed in generally coaxially relationship with the first cylindrical leg and extending out of the housing proximate to the intersection of the first and second legs. The ultrasonic flow cell may have the inlet disposed at an axial extremity of the first leg and the outlet disposed at an axial extremity of the second leg and the first and second legs may be in fluid communication.

In still other forms of the mixing and delivery system for supplying small particles suspended in a liquid to form a slurry for delivery and recirculation includes a mixing tank having an inlet and an outlet; a pump having an inlet and an outlet; a sample cell having an inlet and an outlet; an ultrasonic flow cell having an inlet and an outlet; and a transition bushing having an inlet and an outlet. In some of these embodiments the sample cell may have first and second generally rectangular planar opposed faces, and the inlet of the sample cell may be rectangular and defined by two opposed sides which are respectively part of the first and second generally rectangular planar opposed faces and the opposed sides may be much longer in length than the intermediate opposed sides of the rectangular inlet. The outlet of the mixing tank may be connected to the inlet of the pump and the outlet of the pump may be connected to the inlet of the transition bushing by a circular cross section tube and the transition bushing may be coupled directly to the inlet of the sample cell. The transition bushing may have a tapered construction with the transition bushing tapering at the inlet thereof to the cross-section of the circular cross-section tubing to the rectangular inlet of the sample cell, the transition bushing may be a housing having (1) first and second generally trapezoidal shaped opposed spaced plates which taper from the maximum dimension of the sample cell inlet to the diameter of the tube and (2) two sections of a truncated cone tapering from a maximum circumferential extent proximate the circular cross-section tubing to a point which is closely spaced from the circular cross section tubing, the two sections of a truncated cone are disposed on respective outer faces of the first and second trapezoidal shaped opposed plates and extending outwardly to increase the volume of the transition bushing.

In some forms of the invention the ultrasonic flow cell comprises an ultrasonic probe disposed in a fluid conduit between the sample cell and the mixing tank, the conduit forcing all of the flow from the sample cell to the mixing tank around the ultrasonic probe. The ultrasonic flow cell may comprise a generally cylindrical housing and the ultrasonic probe may be disposed in coaxial relationship with the housing. The mixing tank has a top and a bottom and the bottom being generally conical in some forms of the invention.

The mixing tank may have a generally vertical axis and the outlet of the flow cell includes a generally elongated tube extending into the mixing tank. The tube may have a free end thereof that extends into the mixing tank. The free end may allow fluid flow out of the tube into the mixing tank through a plurality of holes disposed around the side face thereof. The holes in the side face of the tube are disposed in generally axially aligned relationship with the conical portion of the mixing tank in some forms of the invention. In some embodiments the ultrasonic flow cell comprises a generally L-shaped body having first and second generally cylindrical legs and the ultrasonic probe is generally elongated and disposed in generally coaxially relationship with the first cylindrical leg and extends out of the housing proximate to the intersection of the first and second legs.

BRIEF DESCRIPTION OF THE DRAWING

The invention will be better understood by reference to the accompanying drawing in which:

FIGS. 2A and 2B are respectively a plan view and a partially sectional view taken through a vertical plane of the mixing tank in the apparatus of FIG. 1.

FIG. 3 is a partially schematic elevational view of a portion of the sample cell shown in FIG. 1 on which is superimposed a diagrammatic plot of the particle distribution in the visible portion of the sample cell with and without the transition bushing in accordance with one form of the present invention.

DESCRIPTION OF THE PREFERRED EMBODIMENT

Figure 1:
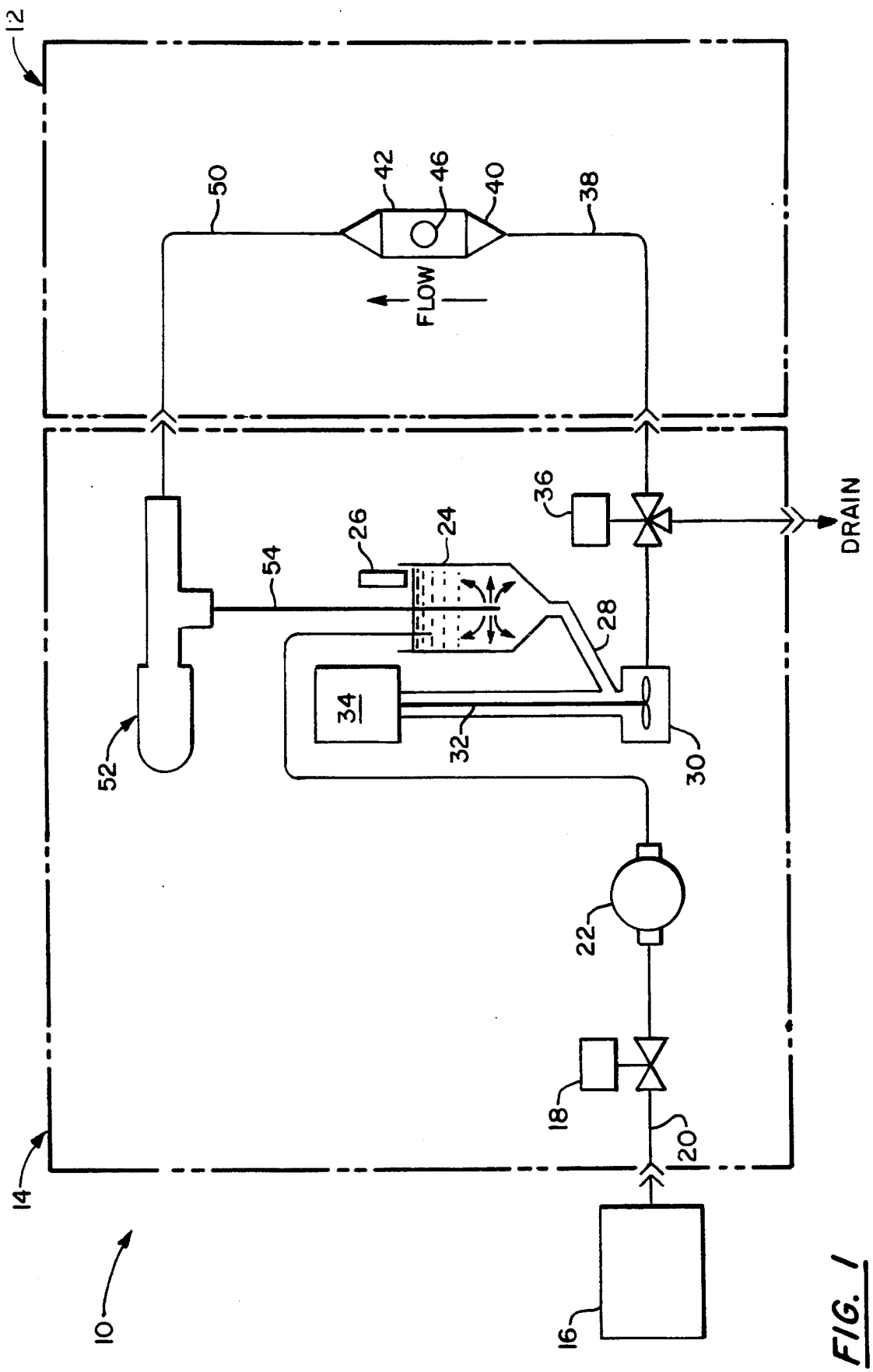
FIG. 1 is a schematic view of the automatic small volume recirculation flow system module and measurement module in accordance with one form of the present invention.

Referring now to FIG. 1 there is shown an automated small volume small mixing and recirculation system for particle analysis 10 consisting of a measurement module 12 and a flow system module 14. The flow system module 14 is fed by a customer's fluid supply 16. The results of the analysis provided by the present apparatus may be used to control a process from which the particles were taken. An electrically actuated valve 18 disposed in the inlet line 20 controls flow to the flow system and particularly to the transfer pump 22. The outlet of the transfer pump 22 is connected to a mixing tank 24 which in the present invention is cylindrical and disposed with the axis thereof in a generally vertical orientation. The transfer pump 22 is controlled by a level sensor 26 that limits the maximum height of the fluid in the mixing tank 24. The mixing tank 24 has an outlet 28 at the lower extremity thereof which connects to a centrifugal pump 30. The pump 30 is driven by a elongated shaft 32 coupled to a variable speed pump motor 34. The length of the shaft 32 is sufficient so that the motor is well above the level of the slurry in the pump 30 and thus avoids the need for shaft seals on the shaft 32.

The output of the pump 30 is directed to a circulate/drain valve 36. This valve 36 permits the alternate draining of the slurry for testing of another sample or passage of the slurry to the measurement module and specifically to the sample cell and transition bushing 40. It is critical for uniform flow that no step up or step down diameters are in the internal flow surfaces. Stated another way, slurry flow through a circular cross section tube to a rectangular cross section sample cell has enormous effects on the distribution of particles across the measurement zone. The circulate/drain valve 36 is a unique two-way valve that was designed so that the open position flow area is the same ID as the tubing and connectors. In the drain position the flow continues around the recirculation loop as the fluids also flow to a drain. In this way particles are not selectively filtered out, which would create a non-uniform distribution. Also, since material distribution is not disturbed by the open valve, a solution can be diluted to a less dense mixture.

The flow of the slurry from the valve 36 to the transition bushing 40 is by means of a tube 38 having an outside diameter in the preferred embodiment of 0.250 inches (0.635 centimeters). In the preferred embodiment the transition bushing 40 players tapers from the cross-section of the interior of the tubing 38 having a 0.250 inch (0.635 centimeters) inside diameter to the cross-section of the interior of the sample cell. Because smooth non-turbulent flow is of great importance it will be understood that the inside dimensions of the transition bushing 40 at the respective ends thereof will exactly mate with respectively the inside of the tubing 38 and the inside of the sample cell 44. More specifically, the preferred embodiment will have no step at the intersection between (1) the interior wall of the sample cell and the interior of the mating end of the transition bushing 40 and (2) the interior wall of the tube 38 and the interior of the mating end of the transition bushing 40.

It will be understood that the sample cell 44 has an outer housing 42 which encloses the actual sample cell 44 and that a portion of the actual sample cell 44 is visible through a window 46 in the housing 42. Sample cell 44 has a generally rectangular cross-section as well as a generally rectangular face. The cross-section of the sample cell 44 is 0.080 by 0.500 inches in the preferred embodiment. It will thus be seen that the transition bushing tapers within the 1.281 inches length thereof from the round cross-section having a .250 inch inside diameter to the uniform cross-section of the sample cell of 0.080 by 0.50 inches. It will be further seen that the transition bushing includes portions which are sections of a truncated cone 40a a and a trapezoidal shaped section 40b. It will be seen from FIG. 4 that the trapezoidal section 40b tapers from the cross-section of the sample cell 44 to the 0.250 diameter of the tubing 38.

Generally the truncated conical shaped portion 40a tapers to a point at the lower most, as viewed, extremity of the sample cell 44. It will be understood that two such sections of a truncated cone 40a are embodied in each transition bushing 40 and that only one section of a truncated cone 40a is visible in FIG. 4. The other section of a truncated cone is disposed on the opposite planar face of the trapezoidal portion 40b.

Testing has established that the fluid flow of the slurry into the sample cell 44 must have a minimum amount of turbulence. The transition bushing 40 in accordance with the present invention avoids that turbulence. More particularly, as best shown in FIG. 3 if the transition from the tubing 38 to the sample cell 44 is made with a conventional fitting the distribution of particles across the width of the sample cell 44 as viewed through the window 46 of the housing 42 is as shown by the curve A. In other words if there is not a smooth transition there is a disproportionate concentration of large particles in the center of the sample cell 44. The transitional area between the tubing inside diameter and the sample cell opening has been designed to uniformly distribute particles across the rectangular cell measurement zone. The length of the transition bushing is designed to decrease the percentage of large particles that cross the fluid streamlines in the sample cell. The transition piece geometry is based on the relaxation time of a 700 micron particle of 10g/cc density in a 10cp fluid exiting from a 0.635 cm diameter tubing.

If the transition bushing 40 in accordance with the illustrated preferred form of the invention is utilized, the distribution is as indicated by the curve B in FIG. 3.

Figure 5:
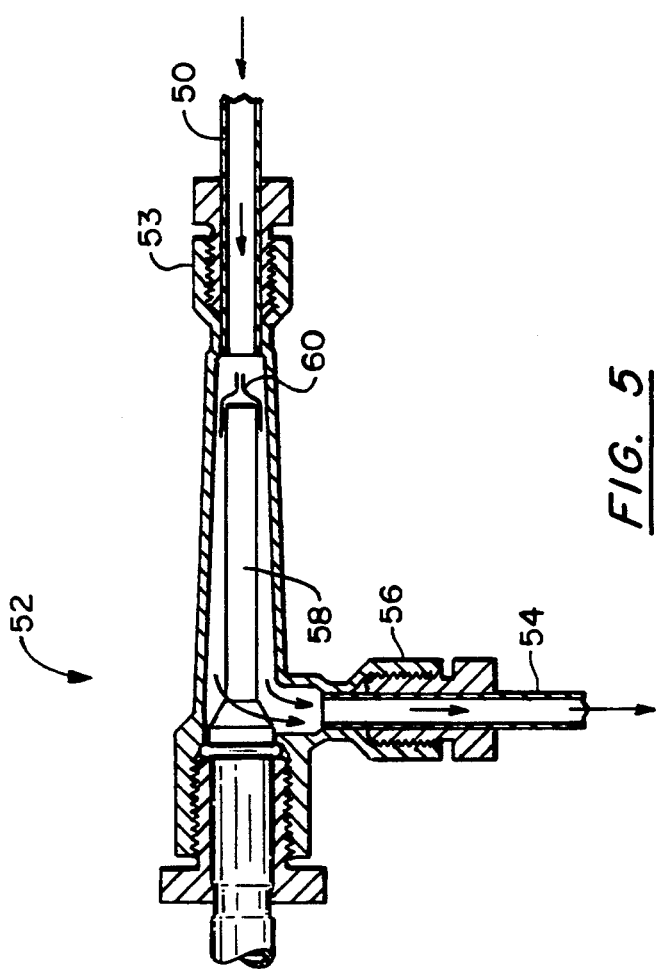
FIG. 5 is an axial cross-section of the ultrasonic flow cell shown in FIG. 1.

The slurry flows from the sample cell 44, into the tube 50, out of the measurement module 12, into the flow system 14 and particularly to the ultrasonic flow cell 52. The ultrasonic flow cell 52 is seen in greater detail in FIG. 5 in which it will be apparent that the flow cell 52 has a generally L-shaped housing which includes a first elongated generally cylindrical portion 53 coupled to the tube 50 and a second elongated generally cylindrical portion 56 disposed at right angles to the first portion 53. An ultrasonic probe 58 is disposed within the first portion 53 of the flow cell 52. More particularly the ultrasonic probe 58 is disposed in coaxial relation with the portion 53 of the housing of the flow cell 52, thus all flow out of the sample cell 44 must pass through the tube 50 into the flow cell 52 and then via the tube 54 into the mixing tank 24. The ultrasonic probe 58 is a 50 W ultrasonic probe that intersects the fluid path and imparts energy to the particles as they flow past the probe tip. One such device is manufactured by Sonics & Materials, Inc. of Danbury, Conn. As the particles reach the vicinity of the probe each particle gets the same energy thus eliminating non uniform conditioning and reducing the heat imparted to the particle.

It will be understood that this arrangement of an in-line ultrasonic probe 58 is unique to the present apparatus. The conventional design approach is to position the ultrasonic probe in the mixing tank. It has been found that the location in line, as in the present, produces better deagglomeration than when the ultrasonic probe is located in the tank and in addition the preferred 50 watt ultrasonic probe has better contact with the slurry flow and imparts a uniform energy to individual particles as they flow past the probe tip 60. Because of the serial or sequential flow of the particles past the tip 60 of the probe each particle receives the same energy and thus eliminates non-uniform particle condition and thereby reduces the total amount of heat imparted to the respective particles. The flow from the flow cell 52 continues through the tube 54 into the mixing tank 24. The tube 54 is provided as best seen in FIG. 2B with six holes disposed in the lower extremity thereof. More particularly, six holes 54a are disposed, in the preferred embodiment, with their centerlines in a common horizontal plane that is perpendicular to the axis of the tube 54. The holes 54a are disposed at equal angular intervals about the tube 54. In other words, the centerlines of the respective radially disposed holes in the tube 54 are disposed at 60 degree intervals about the face of the tube 54. It will be further understood that the lower most extremity of the tube 54 is capped to force all of the fluid passing from the flow cell into the tube 54 to flow outward through one of the six holes 54. As illustrated diagrammatically in FIG. 2B this results in flow paths from the respective holes 54 which extend both upwardly and downwardly for optimum mixing of the slurry. The collective cross-section of the six radial holes 54a has an area equal to the transverse cross-section of the tube 54.

It will be seen that the mixing tank 24 has the lower extremity thereof shaped in a conical form and that the lower most extremity of the tube 54, in which the holes 54a are disposed, is disposed within the conical portion 24a of the mixing tank 24. More particularly the holes 54a are generally centered with respect to the vertical extent of the conical portion 24a of the mixing tank 24.

In operation, the mixing tank 24 is filled to a volume determined by the level sensor 26. The centrifugal pump 30 is activated to begin flow through the system. Particles are then added to the circulating liquid at the mixing tank 24. The mixture of circulating liquid and particles will typically be the slurry that has been referred to in the Background of the Invention section of this application. From there a mixture of particles and liquid is drawn down through the tank stem 28 and into the impeller cavity surrounding the impeller of the pump 30 where it is centrifugally driven into the system tubing. It travels through the circulate/drain valve 36 into the transition bushing 40 and into the sample cell 44 for analysis. Fluid then travels into the ultrasonic flow cell 52 for deagglomeration if necessary and is returned to the mixing tank through the tube 54 and holes 54a.

The present apparatus provides a fully automated mixing and recirculating system with features that mix and recirculate without distortion of particle size distribution. The device uses a non impeller, static return flow mixer in conjunction with a pump. that is designed to avoid the need for a shaft seal. The system components and line connections throughout the circulating loop are designed to prevent particle entrapment and sedimentation. A unique flow transition bushing is utilized in the sample cell area to maintain uniform particle distribution in the sample cell measurement zone. An in-line flow cell with an ultrasonic probe provides particle deagglomeration. The automatic features allow solvent filling, de-aerating, mixing, circulating, ultrasonic conditioning, diluting, rinsing, and draining for continuous automated operation.

Figure 6:
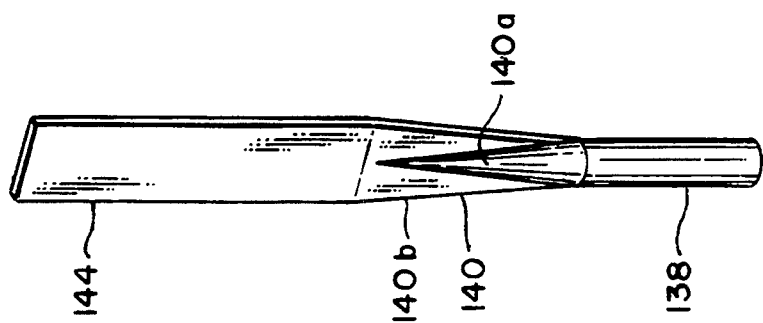
FIG. 6 is a view similar to FIG. 4 showing an alternate embodiment in which the sections of truncated cones are more elongated.
Figure 4:
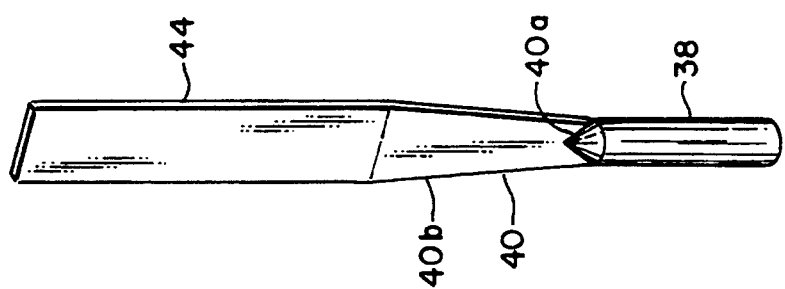
FIG. 4 is a elevational view of transition bushing and sample cell window in accordance with one form of the present invention.

The invention has been described with reference to its illustrated preferred embodiment. Persons skilled in the art of such devices may upon exposure to the teachings herein, conceive other variations. For example, the ultrasonic flow cell 58 may be installed in the tube 38 instead of the location shown herein. Ordinarily, the location in the loop intermediate the sample cell 42 and the mixing tank 24 is preferable because with that arrangement any bubbles formed at the ultrasonic probe tip 60 might be measured as particles in the sample cell 42. The alternate embodiment of the transition bushing shown in FIG. 6 differs from the form shown in FIG. 4 in that the sections of cones are elongated so that they extend almost to the end of the transition bushing proximate to the sample cell 144. It will be understood that this form of the invention is marked with reference numerals that correspond to the reference numerals in Figure except that each is 100 integers higher. Thus the element 144 of FIG. 6 corresponds to element 44 of FIG. 4. Although the form shown in FIG. 6 is advantageous it has been found that the form shown in FIG. 4 is the preferred form of the invention. Such variations are deemed to be encompassed by the disclosure, the invention being delimited only by the following claims.

What is claimed is:

1. A mixing and delivery system for supplying small particles suspended in a liquid to form a slurry for delivery and recirculation which comprises:

a mixing tank having an inlet and an outlet;
a pump having an inlet and an outlet;
a sample cell having an inlet and an outlet;
an ultrasonic flow cell having an inlet and an outlet;
a transition bushing having an inlet and an outlet;
said sample cell having first and second generally rectangular planar opposed faces, said inlet of said sample cell being rectangular and defined by two opposed sides which are respectively part of said first and second generally rectangular planar opposed faces, said opposed sides being much longer in length than the intermediate opposed sides of said rectangular inlet;
said outlet of said mixing tank being connected to said inlet of said pump and said outlet of said pump being connected to said inlet of said transition bushing by a circular cross section tube, said transition bushing being coupled directly to said inlet of said sample cell;
said transition bushing having a tapered construction, said transition bushing tapering at the inlet thereof from the cross-section of said circular cross-section tubing to said rectangular inlet of said sample cell, said transition bushing being formed from (1) a generally trapezoidal shaped portion which tapers from the maximum dimension of said sample cell inlet to the diameter of said tube and (2) two sections of a truncated cone tapering from a maximum circumferential extent proximate said circular cross-section tubing to a point that is disposed in space relation to said circular cross-section tubing.

2. The apparatus as described in claim 1 wherein:
said ultrasonic flow cell comprises an ultrasonic probe disposed in a fluid conduit between said sample cell and said mixing tank, said conduit forcing all of said flow from said sample cell to said mixing tank around said ultrasonic probe.

3. The apparatus as described in claim 2 wherein:
said ultrasonic flow cell comprises a generally cylindrical housing and said ultrasonic probe is disposed in coaxial relationship with said housing.

4. The apparatus as described in claim 3 wherein:
said mixing tank has a top and a bottom, said bottom being generally conical.

5. The apparatus as described in claim 4 wherein:
said mixing tank having a generally vertical axis, said outlet of said flow cell includes a generally elongated tube extending into said mixing tank, said tube having a free end thereof, said free end extending into said mixing tank, said free end allowing fluid flow out of said tube into said mixing tank through a plurality of holes disposed around the side face thereof, said holes in said side face of said tube being disposed in generally axially aligned relationship with said conical portion of said mixing tank.

6. The apparatus as described in claim 5 wherein:
said ultrasonic flow cell comprises a generally L-Shaped body having first and second generally cylindrical legs and said ultrasonic probe is generally elongated and disposed in generally coaxially relationship with said first cylindrical leg and extends out of said housing proximate to the intersection of said first and second legs.

7. The apparatus as described in claim 6 wherein:
said ultrasonic flow cell has said inlet disposed at an axial extremity of said first leg and said outlet disposed at an axial extremity of said second leg, said first and second legs being in fluid communication.

8. A mixing and delivery system for supplying small particles suspended in a liquid to form a slurry for delivery and recirculation which comprises:
a mixing tank having an inlet and an outlet;
a pump having an inlet and an outlet;
a sample cell having an inlet and an outlet;
an ultrasonic flow cell having an inlet and an outlet;
a transition bushing having an inlet and an outlet;
said sample cell having first and second generally rectangular planar opposed faces, said inlet of said sample cell being rectangular and defined by two opposed sides which are respectively part of said first and second generally rectangular planar opposed faces, said opposed sides being much longer in length than the intermediate opposed sides of said rectangular inlet;
said outlet of said mixing tank being connected to said inlet of said pump and said outlet of said pump being connected to said inlet of said transition bushing by a circular cross section tube, said transition bushing being coupled directly to said inlet of said sample cell.

9. The apparatus as described in claim 8 wherein:
said ultrasonic flow cell comprises an ultrasonic probe disposed in a fluid conduit between said sample cell and said mixing tank, said conduit forcing all of said flow from said sample cell to said mixing tank around said ultrasonic probe.

10. The apparatus as described in claim 9 wherein:
said ultrasonic flow cell comprises a generally cylindrical housing and said ultrasonic probe is disposed in coaxial relationship with said housing.

11. The apparatus as described in claim 10 wherein:
said mixing tank has a top and a bottom, said bottom being generally conical.

12. The apparatus as described in claim 11 wherein:
said mixing tank having a generally vertical axis, said outlet of said flow cell includes a generally elongated tube extending into said mixing tank, said tube having a free end thereof, said free end extending into said mixing tank, said free end allowing fluid flow out of said tube into said mixing tank through a plurality of holes disposed around the side face thereof, said holes in said side face of said tube being disposed in generally axially aligned relationship with said conical portion of said mixing tank.

13. The apparatus as described in claim 12 wherein:
said ultrasonic flow cell comprises a generally L-shaped body having first and second generally cylindrical legs and said ultrasonic probe is generally elongated and disposed in generally coaxially relationship with said first cylindrical leg and extends out of said housing proximate to the intersection of said first and second legs.

14. The apparatus as described in claim 13 wherein:
said ultrasonic flow cell has said inlet disposed at an axial extremity of said first leg and said outlet disposed at an axial extremity of said second leg, said first and second legs being in fluid communication.

15. A mixing and delivery system for supplying small particles suspended in a liquid to form a slurry for delivery and recirculation which comprises:
a mixing tank having an inlet and an outlet;
a pump having an inlet and an outlet;
a sample cell having an inlet and an outlet;
an ultrasonic flow cell having an inlet and an outlet;
a transition bushing having an inlet and an outlet;
said sample cell having first and second generally rectangular planar opposed faces, said inlet of said sample cell being rectangular and defined by two opposed sides which are respectively part of said first and second generally rectangular planar opposed faces, said opposed sides being much longer in length than the intermediate opposed sides of said rectangular inlet;
said outlet of said mixing tank being connected to said inlet of said pump and said outlet of said pump being connected to said inlet of said transition bushing by a circular cross section tube, said transition bushing being coupled directly to said inlet of said sample cell;
said transition bushing having a tapered construction, said transition bushing tapering at the inlet thereof to the cross-section of said circular cross-section tubing to said rectangular inlet of said sample cell, said transition bushing being a housing having (1) first and second generally trapezoidal shaped opposed spaced plates which taper from the maximum dimension of said sample cell inlet to the diameter of said tube and (2) two sections of a truncated cone tapering from a maximum circumferential extent proximate said circular cross-section tubing to a point that is closer to said sample cell, said two sections of a truncated cone being disposed on respective outer faces of said first and second trapezoidal shaped opposed plates and extending outwardly to increase the volume of said transition bushing.

16. The apparatus as described in claim 15 wherein: said ultrasonic flow cell comprises an ultrasonic probe disposed in a fluid conduit between said sample cell and said mixing tank, said conduit forcing all of said flow from said sample cell to said mixing tank around said ultrasonic probe.

17. The apparatus as described in claim 16 wherein: said ultrasonic flow cell comprises a generally cylindrical housing and said ultrasonic probe is disposed in coaxial relationship with said housing.

18. The apparatus as described in claim 17 wherein: said mixing tank has a top and a bottom, said bottom being generally conical.

19. The apparatus as described in claim 18 wherein: said mixing tank having a generally vertical axis, said outlet of said flow cell includes a generally elongated tube extending into said mixing tank, said tube having a free end thereof, said free end extending into said mixing tank, said free end allowing fluid flow out of said tube into said mixing tank through a plurality of holes disposed around the side face thereof, said holes in said side face of said tube being disposed in generally axially aligned relationship with said conical portion of said mixing tank.

20. The apparatus as described in claim 19 wherein: said ultrasonic flow cell comprises a generally L-shaped body having first and second generally cylindrical legs and said ultrasonic probe is generally elongated and disposed in generally coaxially relationship with said first cylindrical leg and extends out of said housing proximate to the intersection of said first and second legs.

* * * * *